(12) United States Patent
Barron et al.

(10) Patent No.: US 11,697,834 B2
(45) Date of Patent: Jul. 11, 2023

(54) MODULATION OF GENE EXPRESSION IN A HUMAN BIOREACTOR

(71) Applicant: Maxwell Biosciences, Inc., West Lake Hills, TX (US)

(72) Inventors: Annelise E. Barron, Woodside, CA (US); David Haase, Clarksville, TN (US); Joshua McClure, Westlake Hills, TX (US)

(73) Assignee: Maxwell Biosciences, Inc., Austin, TX (US)

( * ) Notice: Subject to any disclaimer, the term of this patent is extended or adjusted under 35 U.S.C. 154(b) by 612 days.

(21) Appl. No.: 16/773,977

(22) Filed: Jan. 27, 2020

(65) Prior Publication Data

US 2020/0319209 A1 Oct. 8, 2020

Related U.S. Application Data

(60) Provisional application No. 62/797,196, filed on Jan. 25, 2019.

(51) Int. Cl.
  *G01N 33/50* (2006.01)
  *C12Q 1/68* (2018.01)
  *A61K 35/16* (2015.01)

(52) U.S. Cl.
  CPC .............. *C12Q 1/68* (2013.01); *A61K 35/16* (2013.01); *G01N 33/5091* (2013.01); *G01N 33/5094* (2013.01); *C12Q 2560/00* (2013.01)

(58) Field of Classification Search
  CPC ...... C12Q 1/68; C12Q 2560/00; A61K 35/16; G01N 33/5091; G01N 33/5094
  USPC ........................................................... 435/6.1
  See application file for complete search history.

(56) References Cited

PUBLICATIONS

Villeda, S. A. et al. Nature Med. 20, 659-663 (2014). (Year: 2014).*
Conboy, I. M. et al. Nature 433, 760-764 (2005). (Year: 2005).*
Isobe, European Journal of Endocrinology, vol. 153: Issue 1, p. 91-98, Jul. 2005. (Year: 2005).*
Mishan, Mohammad Amir, et al. "Pathogenic Tau Protein Species: Promising Therapeutic Targets for Ocular Neurodegenerative Diseases." Journal of Ophthalmic and Vision Research, vol. 14, No. 4, 2019, pp. 491-505., doi:10.18502/jovr.v14i4.5459.
Chen, Xi, et al. "Roles and Mechanisms of Human Cathelicidin LL-37 in Cancer." Cellular Physiology and Biochemistry, vol. 47, No. 3, 2018, pp. 1060-1073., doi:10.1159/000490183.
Sobajima, S, et al. "Gene Therapy for Degenerative Disc Disease." Gene Therapy, vol. 11, No. 4, 2004, pp. 390-401., doi:10.1038/sj.gt.3302200.

(Continued)

*Primary Examiner* — Christine T Mui
(74) *Attorney, Agent, or Firm* — McDermott Will & Emery

(57) ABSTRACT

A method is provided for treating a recipient with a biological product obtained from at least one donor that may be the same as, or different from, the recipient. The method includes identifying a targeted level of gene expression of a first gene in a biological product to be transferred from at least one donor to a recipient; treating the at least one donor to achieve the targeted level of gene expression of the first gene in the biological product; and transferring the biological product from the at least one donor to the recipient.

20 Claims, 2 Drawing Sheets

(56) References Cited

PUBLICATIONS

Lowry, Malcolm B., et al. "A Mouse Model for Vitamin D-Induced Human Cathelicidin Antimicrobial Peptide Gene Expression." The Journal of Steroid Biochemistry and Molecular Biology, vol. 198, 2020, p. 105552., doi:10.1016/j.isbmb.2019.105552.
Gombart, Adrian F., et al. "A Review of Micronutrients and the Immune System—Working in Harmony to Reduce the Risk of Infection." Nutrients, vol. 12, No. 1, 2020, p. 236., doi:10.3390/nu12010236.
Carl, Hsieh, et al. "Curcumin as a Modulator of Oxidative Stress during Storage: A Study on Plasma." Transfusion and Apheresis Science, vol. 50, No. 2, 2014, pp. 288-293., doi:10.1016/j.transci.2013.12.015.
Whyte, D et al. The Epidemiology of Human Gastrointestinal Infections in the Health Service Executive West (Clare, Limerick, Tipperary North), 2001 to 2007 / R. Monahan . . . [Et Al.]. Health Service Executive (HSE), 2018. Web. Jan. 27, 2020.
Findlay, Emily Gwyer et al. "Exposure to the Antimicrobial Peptide LL-37 Produces Dendritic Cells Optimized for Immunotherapy." OncoImmunology 8.8 (2019): 1608106. Print.
Kuroda, Kengo et al. "The Human Cathelicidin Antimicrobial Peptide LL-37 and Mimics Are Potential Anticancer Drugs." Frontiers in Oncology 5 (2015): 1-10. Print.

Machnicka, Magdalena A. et al. "Modomics: a Database of RNA Modification Pathways—2013 Update." Nucleic Acids Research 41.D1 (2012): 1-6. Print.
Grühn, Daniel, and Neika Sharifian. "Lists of Emotional Stimuli." Emotion Measurement (2016): 145-164. Print.
Abbott, Alison. "Infusions of Young Blood Tested in Patients with Dementia . . . " nature.com. N.p., Nov. 1, 2017. Web. Apr. 2, 2020.
Hanna, P. "Lethal Toxin Actions and Their Consequences." Journal of Applied Microbiology 87.2 (1999): 285-287. Print.
Büchau, Amanda S. et al. "The Host Defense Peptide Cathelicidin Is Required for NK Cell-Mediated Suppression of Tumor Growth." The Journal of Immunology 184.1 (2009): 369-378. Print.
Magalhães, João Pedro De, Michael Stevens, and Daniel Thornton. "The Business of Anti-Aging Science." Trends in Biotechnology 35.11 (2017): 1062-1073. Print.
Ravikumar, Soumya, Carl Hsieh, and Vani Rajashekharaiah. "Prospects of Curcumin as an Additive in Storage Solutions: a Study on Erythrocytes." Turkish Journal of Medical Sciences 46 (2016): 825-833. Print.
Boeckel, Sara R. Van et al. "Cathelicidins and the Onset of Labour." Scientific Reports 9.1 (2019): 1-12. Print.
Xhindoli, Daniela et al. "The Human Cathelicidin LL-37—A Pore-Forming Antibacterial Peptide and Host-Cell Modulator." Biochimica et Biophysica Acta (BBA)—Biomembranes 1858.3 (2016): 546-566. Print.

\* cited by examiner

MODULATION OF GENE EXPRESSION IN A HUMAN BIOREACTOR

CROSS-REFERENCE TO RELATED APPLICATION

This application claims the benefit of U.S. provisional application No. 62/797,196, filed Jan. 25, 2019, having the same title, and having the same inventors, and which is incorporated herein by reference in its entirety.

FIELD OF THE DISCLOSURE

The present disclosure relates generally to gene expression modulation, and more particularly, to systems and methods for inducing targeted gene expression for a physiological or therapeutic purpose.

BACKGROUND OF THE DISCLOSURE

Transfusion of blood products from a donor to a recipient is a common medical procedure, and is frequently employed as an adjunct to surgery or in the treatment of injuries or diseases. In the past, blood transfusions often involved whole blood. At present, however, blood transfusions more commonly involve blood components, such as plasma, red blood cells, white blood cells, platelets and clotting factors.

Some recent research efforts have focused on the effect that the relative ages of the donor and recipient have in blood transfusions. For example, extensive parabiosis experiments were conducted at the University of California (Berkeley) involving surgically conjoined young and old mice. Those studies suggested that the blood from a young mouse may rejuvenate tissues in the heart, muscle and brain of the older mouse. However, it was not clear whether the results of the study were limited to parabiosis settings.

A subsequent study conducted at Alkahest, Inc. (San Carlos, Calif.) considered the effects of giving blood from young donors (aged 18 to 30) to older subjects (aged 54 to 86) suffering from mild to moderate Alzheimer's disease. The trial involved 18 individuals who were given weekly infusions for four weeks. Some of the test subjects were given a saline placebo, while others were given plasma from a young donor. The study found no discernible improvements in cognitive abilities in the subjects treated with young plasma, but did find a significant improvement in their daily living skills.

SUMMARY OF THE DISCLOSURE

In one aspect, a method is provided for treating a recipient with a biological product obtained from at least one donor. The method comprises (a) identifying a targeted level of gene expression of a first gene in a biological product to be transferred from at least one donor to a recipient; (b) treating the at least one donor to achieve the targeted level of gene expression of the first gene in the biological product; and (c) transferring the biological product from the at least one donor to the recipient. In some variations of this embodiment, the recipient may also be the donor. In such embodiments, the donation may be autologous, with some time difference between donation and usage of the donated sample (for instance by infusion, injection, or transplantation).

In another aspect, a method is provided for treating a recipient. The method comprises (a) obtaining portions of a biological product from each of a plurality of donors, wherein each portion of the biological product is characterized by a level of a first targeted gene expression; (b) determining a desired level of the first targeted gene expression in a derived product to be derived from the obtained portions of the biological product; (c) forming the derived product by creating a mixture of the obtained portions of the biological product having the desired level of the first targeted gene expression; and (d) administering the derived product to the recipient.

In a further aspect, a method is provided for treating a recipient with a biological product obtained from at least one donor. The method comprises (a) determining a targeted level of a first gene expression in a biological product to be transferred from at least one donor to a recipient; (b) selecting at least one donor based on the targeted level of the first gene expression in the biological product; and (c) transferring the biological product from the at least one donor to the recipient.

In yet another aspect, a method is provided for treating a subject suffering from cancer. The method comprises diagnosing the subject as suffering from cancer; upregulating CAMP gene expression in a donor; collecting white blood cells from the donor, thereby obtaining collected white blood cells, wherein the collected white blood cells include T cells; and performing CAR (Chimeric Antigen Receptor) T cell therapy on the subject; wherein performing CAR T cell therapy on the subject includes (a) genetically modifying the collected white blood cells, and (b) administering the genetically modified white blood cells to the subject.

DETAILED DESCRIPTION

It has now been found that beneficial effects may be realized in donor/recipient therapies involving the donation of a biological product by modulating one or more gene expressions in the donor prior to donation of the biological product. Without wishing to be bound by theory, it is believed that this approach may be utilized to achieve more optimal levels of one or more therapeutic agents in the biological product (and/or the body or tissues of the recipient) than may be possible without gene expression modulation in the donor.

While this approach may be especially suitable to donors of blood or blood components, it is not limited thereto, and may be applicable to donors of many other biological products. Such biological products may include, without limitation, red blood cells, white blood cells, plateless, plasma, clotting factors, cells, organs or tissues.

Figure 1:
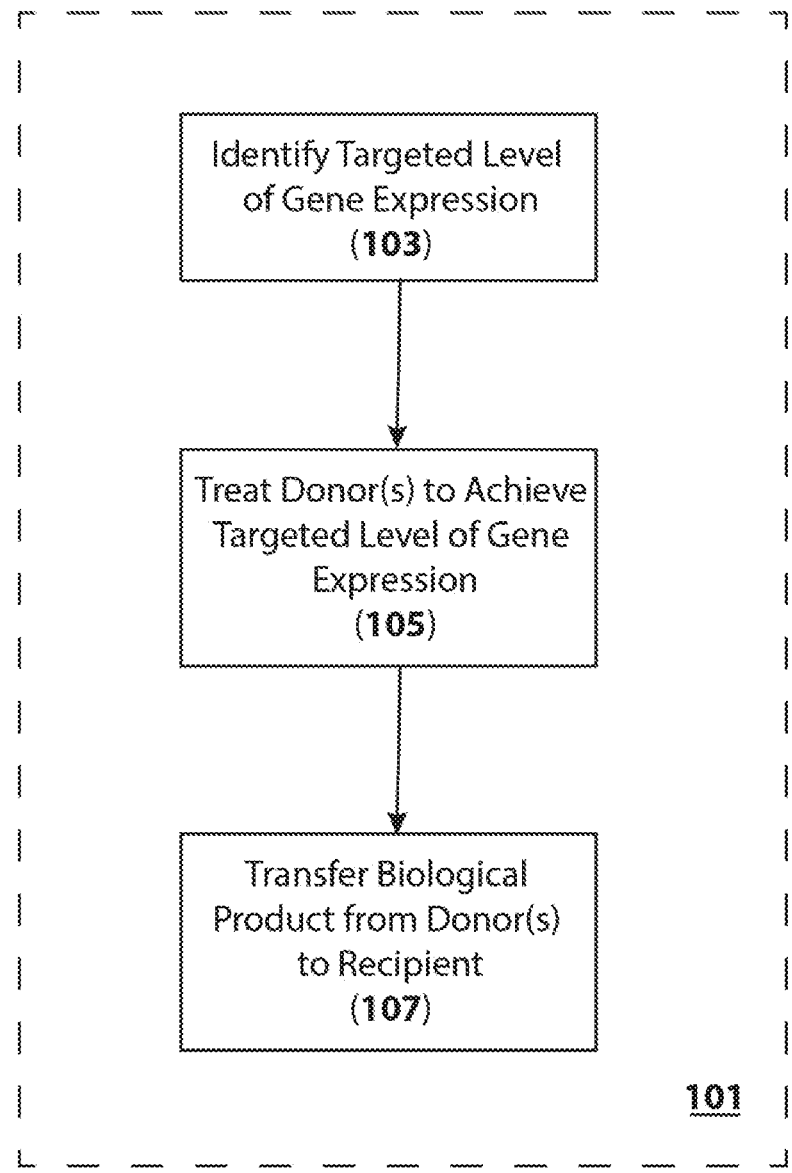
FIG. 1 is an illustration of a particular, non-limiting embodiment of a process in accordance with the teachings herein.

In a preferred embodiment, a method is provided for treating a recipient with a biological product obtained from at least one donor. The method 101, which is summarized in FIG. 1, preferably includes identifying a targeted level of a first gene expression in a biological product to be transferred from at least one donor to a recipient 103. This targeted level of the first gene expression may be determined, for example, from research, or by performing tests (such as, for example, blood tests or assays) on an intended recipient. The at least one donor is then treated with a suitable treatment to achieve the targeted level of the first gene expression in the biological product 105, after which the biological product is transferred from the at least one donor to the recipient 107.

The targeted level of gene expression may consider various factors. For example, in applications in which the biological product is blood plasma, the targeted level of the first gene expression may be based on levels of the first gene expression which will increase the shelf life of peptides or enzymes in the blood plasma.

Various gene expressions and gene expression products may be utilized in the systems and methodologies disclosed herein. These include, without limitation, hormones (including gender-specific hormones such as testosterone and estrogen), antioxidants, protease inhibitors, proteins, metabolites, fatty acids, prostaglandin, alakaloids, peptides, LL-37 and its protein precursor hCAP-18, Proteinase 3, Sirtuin-1, NAD+, BDNF (Brain Derived Neurotrophic Factor), PGC-1a, (Anti-Oxidant Response Element), CoQ10, and GHK.

It will be appreciated that the systems and methodologies disclosed herein are not limited to those involving a single donor. Thus, for example, in some embodiments, one or more pools of donors may be provided. In such embodiments, a biological product may be derived from contributions by individual members of the one or more pools. For example, such a derived biological product may be obtained by blending contributions from individual members of the one or more pools in such a manner as to obtain a derived biological product that has targeted levels of one or more gene expressions. In some embodiments, this approach may be utilized to achieve a gene expression profile or fingerprint consisting of a plurality of gene expressions $G_e \in [G_{e1}, \ldots, G_{en}]$, wherein each $G_i \in G_e$ is a targeted gene expression that may correspond, for example, to a desired numerical range for the gene expression.

It will also be appreciated that the systems and methodologies disclosed herein contemplate the possibility that the donor and recipient may be the same person. For example, in some embodiments, the donation may be autologous. In such embodiments, there may be a time interval between donation and usage of the donated sample, and usage of the donated sample may involve, for example, infusion, injection, or transplantation.

In the systems and methodologies described herein, the donor may be treated in various ways to achieve a targeted level of gene expression. For example, the donor may be given a pharmaceutical composition which may include, for example, resveratrol, niacin, niacinamide, amino acids (such as, for example, 5-HTP (5-Hydroxytryptophan), also known as oxitriptan), mucuna, omega-3 fatty acids (such as, for example, DHA (docosaliexaenoic acid)), alphalipoic acid, sulforaphane, SOD-I, GPx, catalyse, thymosin, butyrate, phenylbutyrate, Vitamin D3, retinoids that may serve as Retinoid X Receptor Agonists, curcuminoids, and various combinatrions or subcombinations of the foregoing. The donor may also undergo suitable treatment or stimuli to induce the formation, in the body of the donor, one or more of the foregoing materials. The donor may also be requested to adhere to a pharmaceutical regiment (such as, for example, taking prescribed pills or capsules over a prescribed time interval), which may involve administration of any of the materials disclosed above; to adopt a prescribed diet, exercise regiment or lifestyle; or to undergo exposure to predetermined stimuli such as, for example, electromagnetic or emotional stimuli.

With respect to the use of emotional stimuli, it is to be noted that direct emotions stimuli are the result of the sensorial stimulus processing by cognitive mechanisms. When an event occurs in an environment and is witnessed by a subject, sensorial stimuli are received by the subject. The cognitive mechanisms process this stimulus and generate the emotional stimulus for each one of the emotions to be affected. Examples of emotional stimuli include, but are not limited to, emotional words, emotional images, emotional faces, and emotional film clips. See, e.g., Grühn, Daniel & Sharifian, Neika (2016), "Lists of Emotional Stimuli", which is incorporated herein by reference.

In some embodiments, the donor may be subjected to genome editing (also known as gene editing) or RNA modification. In such embodiments, DNA may be inserted, deleted, modified or replaced in the genome of the donor. Preferably, such editing will involve targeting genomic modifications to site specific locations.

This may involve, for example, the use of engineered nucleases, or "molecular scissors", to create site-specific double-strand breaks (DSBs) at desired locations in the genome. The induced double-strand breaks may then be repaired through nonhomologous end-joining (NHEJ) or homologous recombination (HR), resulting in targeted mutations or "edits". The engineered nucleases used for this process may include, but are not limited to, meganucleases, zinc finger nucleases (ZFNs), transcription activator-like effector-based nucleases (TALEN), and the clustered regularly interspaced short palindromic repeats (CRISPR/Cas9) system. Examples of possible RNA modification pathways include those described, for example, in Machnicka M A, Milanowska K, Osman Oglou O, et al. MODOMICS: a database of RNA modification pathways—2013 update. Nucleic Acids Res. 2013; 41(Database issue):D262-D267, which is incorporated herein by reference in its entirety.

The donor (or donors) in the systems and methodologies described herein may be selected in accordance with various criteria. These criteria may include, for example, the stipulation that the donor (or donors) are of the same or different sex than the recipient; that the difference in age ($\Delta A$) between the donor(s) and recipient is less than, or greater than, some threshold value; that a gender-specific hormone (which may include, for example, estrogen or testosterone) is absent in or is present in (or present at some specified or minimum level or range in) the donor(s); on the basis of a genomic analysis (which may involve, for example, ascertaining the presence of genomic features in both the donor and the recipient, or may involve choosing a donor based at least partially on the presence of genomic features in the donor that are missing in the recipient); on the presence (or absence) of gene expressions in the donor(s); or on the basis of the metabolics (or relative metabolics) of the donor and recipient. For example, in some applications, it may be desirable to match donors and recipients more closely in age such that, for example, $\Delta A \leq 5$, $\Delta A \leq 3$ or $\Delta A \leq 1$. In other applications, it may be desirable for there to be a significant difference in age between donors and recipients (especially if, for example, the recipient is an elderly person) such that, for example, $\Delta A \geq 10$, $\Delta A \geq 15$ or $\Delta A \geq 20$.

The pharmaceutical compositions utilized in the systems and methodologies disclosed herein may utilize one or more active ingredients (and will preferably utilize multiple active ingredients) which may be dissolved, suspended or disposed in various media. Such media may include, for example, various liquid, solid or multistate media such as, for example, emulsions, gels or creams. Such media may include liquid media, which may be hydrophobic or may comprise one or more triglycerides or oils. Such media may include, but is not limited to, vegetable oils, fish oils, animal fats, hydrogenated vegetable oils, partially hydrogenated vegetable oils, synthetic triglycerides, modified triglycerides, fractionated triglycerides, and mixtures thereof. Triglycerides used in these pharmaceutical compositions may include those selected from the group consisting of almond oil; babassu oil; borage oil; blackcurrant seed oil; black seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; soy oil; glycerol tricaproate; glycerol tricaprylate; glycerol tricaprate; glycerol triundecanoate; glycerol trilaurate; glycerol trioleate; glycerol trilinoleate; glycerol trilinolenate; glycerol tricaprylate/caprate; glycerol tricaprylate/caprate/laurate; glycerol tricaprylate/caprate/linoleate; glycerol tricaprylate/caprate/stearate; saturated polyglycolized glycerides; linoleic glycerides; caprylic/capric glycerides; modified triglycerides; fractionated triglycerides; and mixtures thereof. The use of coconut oil is especially preferred.

Various fatty acids may be utilized in the pharmaceutical compositions disclosed herein. These include, without limitation, both long and short chain fatty acids. Examples of such fatty acids include, but are not limited to, docosahexaenoic acid, caprylic acid, capric acid, lauric acid, butyric acid, and pharmaceutically acceptable salts thereof.

The pharmaceutical compositions disclosed herein may be applied in various manners. Thus, for example, these compositions may be applied as oral, transdermal, transmucosal, intravenous or injected treatments, or via cell-based drug delivery systems. Moreover, these compositions may be applied in a single dose, multi-dose or controlled release fashion.

The pharmaceutical compositions disclosed herein may be manufactured as tablets, liquids, gels, foams, ointments or powders. In some embodiments, these compositions may be applied as microparticles or nanoparticles.

In some embodiments, the pharmaceutically acceptable compositions disclosed herein preferably include a mixture of at least four more preferably at least five, and most preferably at least six materials (preferably active materials) selected from the group consisting of phenylbutyrate, bexarotene, curcumin, resveratrol, retinol, cholecalciferol, fatty acids, and pharmaceutically acceptable salts thereof. In other embodiments, the pharmaceutically acceptable compositions disclosed herein preferably include a mixture of at least four more preferably at least five, and most preferably at least six materials (preferably active materials) selected from the group consisting of phenylbutyrate, bexarotene, curcumin, resveratrol, retinol, phenylbutyrate, cholecalciferol, docosahexaenoic acid, caprylic acid, capric acid, lauric acid, and pharmaceutically acceptable salts thereof.

Various counterions may be utilized in forming pharmaceutically acceptable salts of the materials disclosed herein. One skilled in the art will appreciate that the specific choice of counterion may be dictated by various considerations. However, the use of sodium and hydrochloride salts may be preferred in some applications.

While the systems, methodologies and compositions disclosed herein may be utilized to treat human subjects, it will be appreciated that these systems, methodologies and compositions may also be utilized to treat non-human subjects. In particular, it is contemplated that these systems, methodologies and compositions may find use in treating animal subjects in veterinary applications, or in research or laboratory settings.

The systems and methodologies disclosed herein have various applications. For example, Findlay et al., "Exposure to the antimicrobial peptide LL-37 produces dendritic cells optimized for immunotherapy", OncoImmunology (2019), shows that dendritic cells exposed to LL-37 become potentiated to be ideal for infusion to enhance the effectiveness of CAR T cell therapy. This is an important approach for cancer treatment that is currently in development. However, in the approach of Findlay et al., the dendritic cells were treated exogenous to the body. In accordance some embodiments of the methodologies disclosed herein, the CAMP gene may be upregulated within the body of a donor (which may be the same as, or different from the patient), which would affect the phenotype of the "donor's" endogenous dendritic cells. These cells may then be utilized for treatment.

More specifically, in embodiments of the methodologies disclosed herein, CAMP gene expression may be upregulated in a donor. White blood cells (including T cells) may be collected from that donor, and these white blood cells may be genetically transformed or modified through CAR (Chimeric Antigen Receptor) T cell therapy (this therapy typically involves the addition of the gene for a special receptor that binds to a certain protein on the patient's cancer cells) to cause the T cells to recognize or be receptive to particular markers or cellular ligands that may be present on cancer cells. Such markers may include, for example, PD-1 or PD-L1 (PD-1 is a protein found on T cells that regulates the body's immune responses in that, when it is bound to PD-L1 (another protein), it helps keep T cells from killing other cells, including cancer cells). The subject may then be treated using the methodologies disclosed herein for upregulating CAMP gene expression, after which the modified CAR T cells may be reinfused into the subject (here, it is noted that upregulated endogenous LL-37 expression will preferably have activated the subject's dendritic cells in such a way that CAR T cell therapy may work better). In other words, in this particular embodiment, if the donor is the subject, then the subject is treated to unregulated CAMP gene both before and after the steps of removing T cells and then re-infusing transgenic CAR T cells.

The conventional CAR T cell therapy accomplishes two objectives. First of all, the T cells are genetically altered so that they are receptive to the particular markers (e.g., PD-1 or PD-L1) found on cancer cells. Secondly, the T cells are propagated in culture so there is a greater number of them. Hence, the success of the therapy is premised on the T cells being focused on killing cancer cells in a subject, and on there being more of them. The paper by Findlay et al. shows that T cells propagate more efficiently when exposed to LL-37 (although, as previously noted, in the approach of Findlay et al., the dendritic cells were treated exogenous to the body).

However, it has now been discovered that LL-37 induction may be utilized in a donor prior to CAR T cell therapy so that, when the resulting T cells are collected from the donor, they are better primed to propagate efficiently. It has further been discovered that LL-37 induction may be utilized in a recipient prior to the point when the expanded (propagated) T cells generated from the CAR T cell therapy are administered to or infused into the body of the recipient. This second LL-37 induction serves to activate the dendritic cells, which activate the cytotoxic T cells.

Upregulation of LL-37 typically lasts, at most, about 24 hours. In a typical CAR T cell therapy, there is a 2-4 week interval between the time when the T cells are harvested, and the time when the genetically transformed T cells are returned or reinfused to the subject. With the first LL-37 induction, it is preferred that the white blood cells are harvested within 12 hours of when the first LL-37 induction occurs (that is, within 12 hours of the time at which a pharmaceutical composition is administered to the subject which upregulates LL-37).

It is preferred that the second LL-37 induction occurs within 24 hours before, and more preferably within 10 hours before, the time when the T cells are returned or reinfused to the subject. More preferably, the second LL-37 induction occurs within 6 hours, even more preferably within 4 hours, and most preferably within 3 hours, before the time when the T cells are returned or reinfused to the subject.

The CAR T cell therapy may target the CD19 antigen. It may be utilized, within the context of the systems and methodologies disclosed herein, to treat various cancers including, without limitation, relapsed/refractory B-cell precursor acute lymphoblastic leukemia (ALL) and relapsed/refractory diffuse large B-cell lymphoma (DLBCL).

The systems and methodologies disclosed herein may effectively utilize any of the generations of CARs developed to date. Thus, in some embodiments, the CAR may include an extracellular binding domain, a hinge region, a transmembrane domain, and at least one intracellular signaling domain. In other embodiments, the CAR may include at least one co-stimulatory domain, which may be selected, form example, from the group consisting of CD28, 4-1BB, CD28-41BB and CD28-OX40. In still other embodiments, the CAR may include at least one cytokine selected from the group consisting of IL-2, IL-5 and IL-12.

Figure 2:
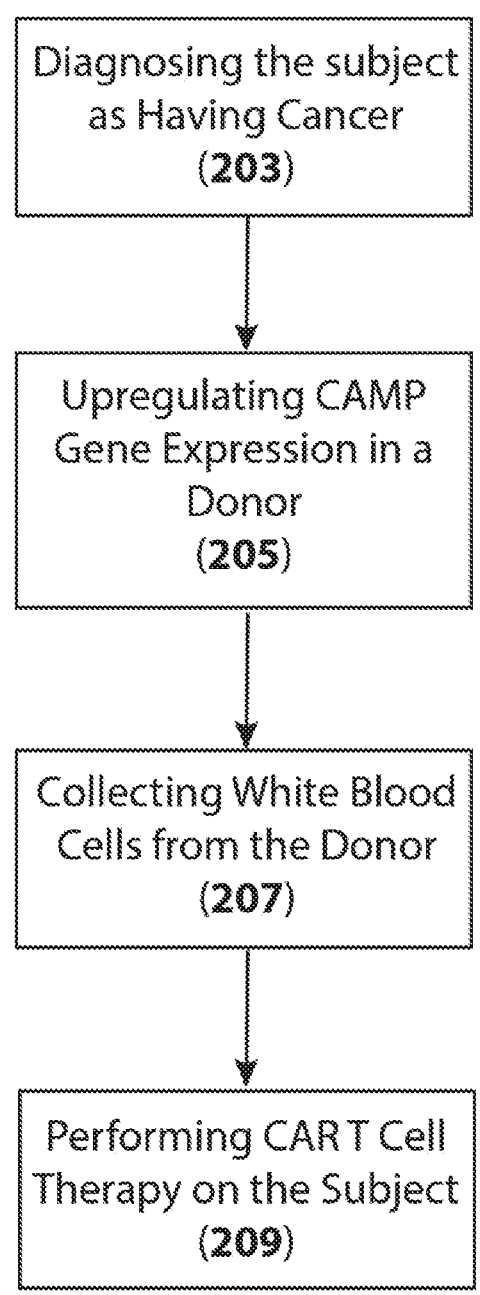
FIG. 2 is an illustration of another particular, non-limiting embodiment of a process in accordance with the teachings herein.

The foregoing methodology is summarized in FIG. 2. As seen therein, a preferred embodiment of the methodology 201 includes diagnosing a subject as having cancer 203. Then, CAMP gene expression is upregulated in a donor 205 (which may be the same as, or different from, the subject) using the methodologies disclosed herein. White blood cells are then collected 207 from the donor and are utilized in performing CAT T cell therapy on the subject 209, which will typically include (a) genetically modifying the collected white blood cells, and (b) administering the genetically modified white blood cells to the subject.

Another application of the systems, methodologies and compositions disclosed herein relates to the treatment of a recipient with a biological product (such as blood, blood plasma or cells) obtained from a donor. In some embodiments, the donor and recipient may be the same. In other embodiments, the donor may include a plurality of donors. In this application, the CAMP gene is upregulated in the donor(s) before the biological product is collected. The collected biological product may then be infused into the recipient. In some embodiments, there may be a significant age difference between the recipient and the donor(s).

Another application of the systems, methodologies and compositions disclosed herein relates to the treatment of recipients having degenerative conditions. Such degenerative conditions may include, but are not limited to, Alzheimer's disease, amyotrophic lateral sclerosis (ALS, Lou Gehrig's disease), cancers, Charcot-Marie-Toothdisease (CMT), chronic traumatic encephalopathy, cystic fibrosis, certain cytochrome c oxidase deficiencies (these may be the cause, for example, of degenerative Leigh syndrome), degerative disc disease (DDD), Ehlers-Danlos syndrome, fibrodysplasia ossificans progressive, Friedreich's ataxia, frontotemporal dementia (FTD), certain cardiovascular diseases (for example, atherosclerotic diseases such as coronary artery disease or aortic stenosis), Huntington's disease, infantile neuroaxonal dystrophy, keratoconus (KC), keratoglobus, leukodystrophies, macular degeneration (AMD), Marfan's syndrome (MFS), certain mitochondrial myopathies, mitochondrial DNA depletion syndrome, multiple sclerosis (MS), multiple system atrophy, muscular dystrophies (MD), neuronal ceroid lipofuscinosis, Niemann-Pick diseases, osteoarthritis, osteoporosis, Parkinson's disease, pulmonary arterial hypertension, prion diseases (such as, for example, Creutzfeldt-Jakob disease or fatal familial insomnia), progressive supranuclear palsy, retinitis pigmentosa (RP), rheumatoid arthritis, psoriatic arthritis, plaque psoriasis, lupus nephritis, lupus erythematosus, Sandhoff Disease, spinal muscular atrophy (SMA, motor neuron disease), subacute sclerosing panencephalitis, Tay-Sachs disease, and various forms of degenerative dementia.

A specific example of the use of the systems, methodologies and compositions disclosed herein in treating a degenerative condition (Alzheimer's disease) may be appreciated with respect to commonly assigned U.S. Ser. No. 16/038,158, now published as U.S. 2019/0015361 (Barron et al.), "POLYTHERAPY MODULATING CATHELICIDIN GENE EXPRESSION MODULATION FOR THE TREATMENT OF ALZHEIMER'S DISEASE AND OTHER CONDITIONS", which is incorporated herein by reference in its entirety. There, a polytherapy of orally available compounds is disclosed that synergistically modulates and induces the expression of the cathelicidin gene (CAMP), which encodes the host defense peptide LL-37. By providing a number of different CAMP-inducing compounds together at the same time, stronger gene induction is achieved than with just one or two compounds, because the mechanism of induction broadens. The approach of the '158 application may be applied in accordance with the teachings herein by having a donor (or donors) of a biological product (for example, blood or blood plasma) undergo the polytherapy described in the '158 application prior to donation to induce the expression of the LL-37 peptide. The polytherapy will preferably be administered within 10 hours of the donation, more preferably within 3-6 hours of the donation, and most preferably within 3-4 hours of the donation. In some cases, the recipient may also undergo the polytherapy, preferably within the same or similar time frame as the donor(s). This approach may ensure elevated levels of the LL-37 peptide in the body of the recipient post-infusion.

One skilled in the art will appreciate that the gene expression (and targeted level of that gene expression) that will be appropriate in treating a degenerative condition will depend on the particular disease or condition being treated. By way of example, although the precise pathophysiology of DDD is not fully understood, the progressive decline in aggrecan (the primary proteoglycan of the nucleus pulposus) appears to be implicated in the disease. Consequently, imbalance in the synthesis and catabolism of certain critical extracellular matrix components may be mitigated by the transfer of genes to intervertebral disc cells encoding factors that modulate synthesis and catabolism of these components.

Another application of the systems, methodologies and compositions disclosed herein relates to the treatment of recipients having toxigenic conditions. Examples of toxigenic conditions include, but are not limited to, diphtheria, anthrax infections and *Clostridium difficile* infections (CDI). These conditions may involve various pathogens such as, for example, *C. ulcerans, A. flavus, B. anthracis, Corynebacterium* and *C. difficile*.

Another application of the systems, methodologies and compositions disclosed herein relates to the treatment of recipients having pathogenic conditions. Examples of pathogenic conditions include, but are not limited to, ocular neurodegenerative diseases (such as, for example, AMD, glaucoma/ocular hypertension, and diabetic retinopathy), including those involving the pathogenic tau protein.

The destructive effects of the pathogenic form of tau can be exerted by several forms of tau such as soluble oligomers, insoluble aggregates, or even by cis p-tau which is an early driver of pathogenic tau. Hence, targeted therapy based on pathogenic tau could be a promising therapeutic for patients with CNS or ocular neurodegeneration, to not only prevent the more destructive effects of pathogenic tau, but also restore normal functioning to neural cells.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims.

What is claimed is:

1. A method for treating a recipient with a biological product obtained from at least one donor, comprising:
    identifying a targeted level of gene expression of a first gene in a biological product to be transferred from at least one donor to a recipient;
    treating the at least one donor to achieve the targeted level of gene expression of the first gene in the biological product; and
    transferring the biological product from the at least one donor to the recipient.

2. The method of claim 1, wherein the biological product is blood plasma.

3. The method of claim 1, wherein the biological product is a human organ.

4. The method of claim 1, wherein said at least one donor is exactly one donor.

5. The method of claim 1, wherein said at least one donor is a plurality of donors.

6. The method of claim 1, further comprising:
    selecting the at least one donor in accordance with the criteria that the at least one donor and the recipient are of the same sex.

7. The method of claim 1, further comprising:
    selecting the at least one donor in accordance with the criteria that the at least one donor and the recipient have an age difference $\Delta A$ (in years), wherein $\Delta A \leq 5$.

8. The method of claim 1, further comprising:
    selecting the at least one donor in accordance with the criteria that the at least one donor and the recipient have an age difference $\Delta A$ (in years), wherein $\Delta A \leq 3$.

9. The method of claim 1, further comprising:
    selecting the at least one donor in accordance with the criteria that the at least one donor and the recipient have an age difference $\Delta A$ (in years), wherein $\Delta A \leq 1$.

10. The method of claim 1, further comprising:
    selecting the at least one donor in accordance with the criteria that the at least one donor and the recipient have an age difference $\Delta A$ (in years), wherein $\Delta A \geq 10$.

11. The method of claim 1, further comprising:
    selecting the at least one donor in accordance with the criteria that the at least one donor and the recipient have an age difference $\Delta A$ (in years), wherein $\Delta A \geq 15$.

12. The method of claim 1, further comprising:
    selecting the at least one donor in accordance with the criteria that the at least one donor and the recipient have an age difference $\Delta A$ (in years), wherein $\Delta A \geq 20$.

13. The method of claim 1, further comprising:
    performing a genomic analysis on the recipient and on the at least one donor;
    identifying genomic features in the recipient and the at least one donor based on the genomic analyses; and
    selecting the at least one donor in accordance with the criteria that the identified genomic features in the recipient and the at least one donor match.

14. The method of claim 1, further comprising:
    performing a genomic analysis on the recipient and on the at least one donor;
    identifying genomic features in the recipient and the at least one donor based on the genomic analyses; and
    selecting the at least one donor in accordance with the criteria that the recipient is missing genes that are present in the at least one donor.

15. The method of claim 1, further comprising:
    selecting the at least one donor in accordance with the criteria that includes the presence of at least one gender specific hormone in the at least one donor.

16. The method of claim 15, wherein the criteria further includes specified levels for the at least one gender specific hormone.

17. The method of claim 16, wherein the specified levels include specified minimum levels for the at least one gender specific hormone.

18. The method of claim 17, wherein the specified levels include specified ranges for the at least one gender specific hormone.

19. The method of claim 16, wherein the at least one hormone includes estrogen.

20. The method of claim 16, wherein the at least one hormone includes testosterone.

* * * * *